(12) United States Patent
Liu et al.

(10) Patent No.: US 10,144,951 B2
(45) Date of Patent: Dec. 4, 2018

(54) METHOD AND MATERIALS TO DEPLETE IMPURITIES FOR EXTRACTION AND PURIFICATION OF NUCLEIC ACIDS FROM STOOL

(71) Applicants: Yiding Liu, Twinsburg, OH (US); Baochuan Guo, Solon, OH (US)

(72) Inventors: Yiding Liu, Twinsburg, OH (US); Baochuan Guo, Solon, OH (US)

(73) Assignee: GLC Biotechnology, Inc., Hudson, OH (US)

( * ) Notice: Subject to any disclaimer, the term of this patent is extended or adjusted under 35 U.S.C. 154(b) by 327 days.

(21) Appl. No.: 14/713,250

(22) Filed: May 15, 2015

(65) Prior Publication Data

US 2016/0333393 A1 Nov. 17, 2016

Related U.S. Application Data

(60) Provisional application No. 61/994,977, filed on May 18, 2014.

(51) Int. Cl.
| | | |
|---|---|---|
| *C12Q 1/68* | (2018.01) | |
| *C12P 19/34* | (2006.01) | |
| *C12Q 1/6806* | (2018.01) | |
| *C12N 15/10* | (2006.01) | |

(52) U.S. Cl.
CPC ....... *C12Q 1/6806* (2013.01); *C12N 15/1003* (2013.01); *C12N 15/1013* (2013.01)

(58) Field of Classification Search
None
See application file for complete search history.

(56) References Cited

U.S. PATENT DOCUMENTS

| | | | |
|---|---|---|---|
| 2012/0208189 A1* | 8/2012 | Xu | C07H 21/02 435/6.11 |
| 2012/0285900 A1 | 11/2012 | Domanico et al. | |
| 2012/0288868 A1 | 11/2012 | Bruinsma et al. | |
| 2012/0288957 A1 | 11/2012 | Bruinsma et al. | |
| 2014/0024036 A1* | 1/2014 | Wang | C12Q 1/6886 435/6.12 |

OTHER PUBLICATIONS

Ahern (The Scientist 9 (15), 20 (1995)).*
Atsushi Akane et al., "Indentification of the Heme Compund Copurified with Deoxyribonucleic Acid (DNA) from Bloodstains, a Major Inhibitor of Polymerase Chain Reaction (PCR) Amplification", Journal of Forensic Sciences, JFSCA, vol. 39, No. 2, Mar. 1994, pp. 362-372.
Carol A. Kreader, "Relief of Amplification Inhibition in PCR with Bovine Serum Albumin or T4 Gene 32 Protein", Applied and Environmental Microbiology, Mar. 1996, vol. 62, No. 3, p. 1102-1106.
Waleed Abu Al-Soud et al., "Purification and Characterization of PCR-Inhibitory Components in Blood Cells", Journal of Clinical Microbiology, Feb. 2001, p. 485-493.

* cited by examiner

*Primary Examiner* — James Martinell

(57) ABSTRACT

Provided herein is materials and method relating to nucleic acids extraction and purification from biological samples such as stool. In particular, binding protein(s) is used to facilitate the extraction and purification of nucleic acids from stool samples, more specifically, depleting and blocking inhibitors and impurities from stool samples and resulting in a highly concentrated and purified nucleic acids preparation.

10 Claims, 1 Drawing Sheet

Specification includes a Sequence Listing.

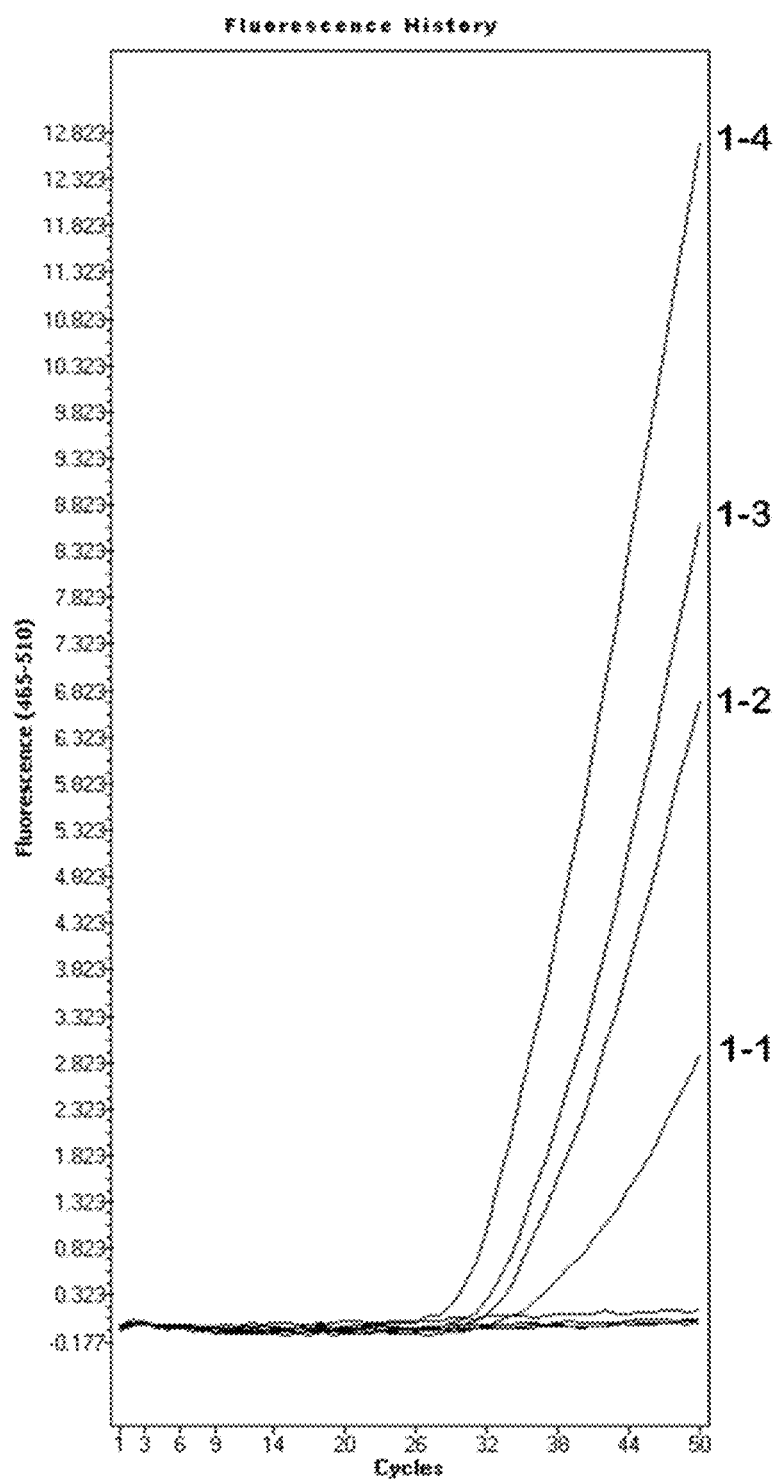

SEQUENCE LISTING

<160> NUMBER OF SEQ ID NOS: 2

<210> SEQ ID NO 1
<211> LENGTH: 20
<212> TYPE: DNA
<213> ORGANISM: Homo sapiens

<400> SEQUENCE: 1 ttgcttttc ccagatgagc                                        20

<210> SEQ ID NO 2
<211> LENGTH: 20
<212> TYPE: DNA

```
<213> ORGANISM: Homo sapiens

<400> SEQUENCE: 2
acactccaag gccgctttac                                                      20
```

METHOD AND MATERIALS TO DEPLETE IMPURITIES FOR EXTRACTION AND PURIFICATION OF NUCLEIC ACIDS FROM STOOL

CROSS-REFERENCE TO RELATED APPLICATION

The present application claims priority to and the benefit of U.S. provisional patent application number U.S. 61/994,977 filed May 18, 2014, the entire disclosure of which is incorporated herein by reference.

FIELD OF INVENTION

The invention relates generally to assays that analyze nucleic acid markers for detecting cancer and other diseases, and more particularly, to the extraction and purification of nucleic acids from stool samples by depleting impurities, for use in these assays.

BACKGROUND OF THE INVENTION

Fecal DNA testing, based on enzymatic-based analysis of disease-derived DNA in stool, has been emerging as an alternative method for colorectal cancer screening because of its non-invasive, highly sensitive, and patient friendly nature. However, stool posted challenges to enzymatic-based analysis because it contains vast amounts of interfering substances that prevent effective DNA extraction and purification, as well as inhibitors that inhibit enzymatic manipulation of DNA, for example, amplification by polymerase chain reaction (PCR). In other words, stool contains a very large amount of impurities (interfering substances and inhibitors).

Stool comprises debris from foods and numerous metabolites from digestion. While solid matter can be removed with centrifugation, soluble impurities remain in solution containing nucleic acids. Cancer related DNA alterations only comprise a small portion of total stool DNA retrieved. Detecting these rare events requires preparation of highly concentrated DNA so that enough amounts of DNA can be loaded (used) into enzymatic-based analysis assays like PCR.

The methods that are currently used for DNA extraction and purification include alcohol precipitation, binding of nucleic acids to silica in the presence of chaotropic salts, gel filtration, anion exchange, and sequence-specific capture. However, they are not effective in preparing highly concentrated, highly purified DNA from stool, especially from a large stool sample. For example, some inhibitors in stool can be co-isolated along with DNA by these methods because the amount of these inhibitors in stool is so large that the methods for DNA extraction just cannot completely remove them. When DNA is concentrated, these inhibitors are concentrated too, inhibiting enzymatic-based analysis assays and therefore leading to a failure of detecting DNA biomarker from stool. Clearly, to use DNA retrieved from stool as a cancer biomarker, it is important that the amount of inhibitors must be minimized, i.e., they should be present in very low concentrations, which will not inhibit enzymatic-based analysis assays even when highly concentrated DNA prepared from a large stool sample are used for analysis.

One solution to this problem is to remove these impurities as much as possible by other means before or during the process of extracting DNA. Prior art methods include cetyl trimethylammonium bromide (CTAB) treatment, phenol/chloroform extraction, protease treatment, and other inhibitor binding/removing procedures such as the PPVP treatment procedure. However, these prior art methods are either not effective or too complicated to use when DNA is extracted from a large amount of stool.

This current invention is designed to address the issue related to removal of the interfering substances and inhibitors from stool for preparation of highly concentrated, highly purified stool DNA. In one method provided, the binding protein(s) that binds to impurities is added to the stool sample before or during the process of extracting DNA. As a result, these bound impurities are not co-isolated with DNA and will not interfere with DNA extraction as well. In another method provided, the method of using the binding protein(s) to remove impurities is combined with a method using a pre-treatment buffer to further improve the effectiveness of removing the impurities from stool.

SUMMARY OF THE INVENTION

Herein, the present invention provides methods and a kit to deplete impurities in stool samples containing nucleic acids, making it possible to prepare highly concentrated, highly purified nucleic acids from stool for enzymatic-based analysis. The technology is directed to minimize the amount of impurities in a nucleic acid preparation. For example, the methods provide technologies for depleting the impurities before and during the process of preparing purified nucleic acid from stool so that the resulted nucleic acids preparation is highly concentrated for enzymatic-based analysis, while having minimum amounts of the inhibitors that inhibit the analysis.

This invention is particularly useful for fecal DNA testing, wherein said fecal DNA testing requires extraction of purified DNA from stool, followed by analysis of DNA retrieved. One application of fecal DNA testing is colorectal cancer screening. Fecal DNA testing is based on the detection of the DNA biomarker in stool by enzymatic-based analysis and therefore both the quantity and quality (purity) of fecal DNA retrieved are essential to the analysis. The current invention is also useful for isolation of other nucleic acids such as various forms of RNA from stool.

This invention provides a method for improving preparation of purified nucleic acids from a stool sample, which comprises step of using binding protein(s) to deplete impurities in said stool sample, wherein the binding protein(s) is added to and mixed with the stool sample before or during the process of preparing purified nucleic acids. In some preferred embodiments, the binding protein(s) can bind the impurities in stool. Because the bound impurities are now carried by the binding protein(s), fewer impurities will interfere with preparation of nucleic acids from stool. In the same way, fewer impurities will be co-isolated with nucleic acids during the process of extracting nucleic acids from stool, making it possible to preparing highly concentrated, highly purified nucleic acids from stool. In another embodiment, the binding protein(s) is any protein that can bind the impurities in stool, but itself will not interfere with the process of extracting nucleic acids from stool. In some embodiments, said binding protein(s) includes, but not limited to, albumin, acetylated albumin, bovine serum albumin (BSA), human serum albumin (HSA), casein, beta casein, T4 gene 32 protein (gp32), or any combination of them. In another embodiment, said nucleic acids are DNA, mRNA, fRNA, tRNA, miRNA, small interfering RNA (sRNA), or any combination of them. In some embodiments, the method provided further comprises preparation of purified nucleic acids from stool, wherein methods for said preparation of purified nucleic acids from stool include, but not limited to, sequence specific capture, carboxylate-modified magnetic beads capture, silica-based nucleic acid extraction and purification, alcohol precipitation, or any combination of them.

This invention also provides a method of preparing purified DNA from stool sample, comprising steps of (a) treating said stool sample with a pre-treatment buffer before extraction of DNA from stool; (b) using binding protein(s) to deplete impurities in said stool sample before, during, or after said step of treating said stool; and (c) extracting target DNA sequences by sequence specific capture after said step of treating stool with a pre-treatment buffer.

In some preferred embodiments, said step of treating said stool sample comprises mixing and incubating said stool sample with said pre-treatment buffer to precipitate the impurities in stool, followed by centrifugation to pellet any precipitates and stool solid matter (if present), yielding supernatant that contains nucleic acids, but less amounts of said impurities. Then, supernatant is separated from the pellet by transferring the supernatant to another tube (liquid container), from which DNA is extracted. In some embodiments, said pre-treatment buffer contains a combination of acetate salts and guanidine thiocyanate; wherein the preferred final concentration of said acetate salts is 50 mM or more, 100 mM or more, and 200 mM or more after mixing said pre-treatment buffer with said stool sample. In another embodiment, the preferred final concentration of said guanidine thiocyanate is 2.0M or more after mixing said pre-treatment buffer with said stool sample.

In another preferred embodiment, said step of using binding protein(s) to deplete impurities in said stool sample comprises adding said binding protein(s) to and mixing said binding protein(s) with said stool sample. In some embodiments, said step of using binding protein(s) to deplete impurities in said stool sample takes place before, during, or after said step of treating said stool sample with said pre-treatment buffer. In some preferred embodiments, the binding protein(s) can bind the impurities in stool. Because the bound impurities are now carried by the binding protein(s), fewer impurities will interfere with preparation of nucleic acids from stool. In the same way, fewer impurities will be co-isolated with nucleic acids during the process of extracting nucleic acids from stool, making it possible to preparing highly concentrated, highly purified nucleic acids from stool. In another embodiment, the binding protein(s) is any protein that can bind the impurities in stool, but the protein(s) itself will not interfere with the process of extracting nucleic acids from stool. In some embodiments, said binding protein(s) includes, but not limited to, albumin, acetylated albumin, bovine serum albumin (BSA), human serum albumin (HSA), casein, beta casein, T4 gene 32 protein (gp32), or any combination of them. In a preferred embodiment, said binding protein(s) is bovine serum albumin (BSA), wherein the preferred amount of said BSA is 1 mg or more per 1 mL said stool sample; wherein another preferred amount of said BSA is 5 mg or more per 1 mL said tool sample; wherein another preferred amount of said BSA is 10 mg or more per 1 mL said treated stool sample; wherein another preferred amount of said BSA is 11.25 mg or more per 1 mL said treated stool sample.

In another embodiment, said step of extracting target DNA sequences is achieved by sequence specific capture after said step of treating stool with a pre-treatment buffer. In some embodiment, said sequence specific capture is achieved with said pre-treatment buffer as the hybridization buffer. As a result, no additional solution is needed for hybridization, reducing the volume of the stool solution, from which DNA is extracted.

Furthermore, herein is provided a kit for depleting/blocking impurities in stool, the kit comprising a stool pre-treatment and hybridization buffer, inhibitor depleting/blocking protein(s) (binding proteins), tubes and instructions of use. Various type of containers, tubes are available for inclusion in a kit, for example those commercially available from a number of suppliers.

Additional embodiments will be apparent to persons skilled in the relevant art based on the teachings contained herein.

BRIEF DESCRIPTION OF FIGURES

FIG. 1. Real-time PCR amplification curves for quantification of stool DNA (a sequence of human ACTB gene) extracted in the presence of different concentrations of BSA. Buffer A is a pre-treatment buffer containing acetate salt and guanidine thiocyanate, which also served as the hybridization buffer for sequence-specific capture of the ACTB sequences.
1-1 Stool sample treated with Buffer A, but without BSA
1-2 Stool sample treated with Buffer A and 1 mg/mL BSA
1-3 Stool sample treated with Buffer A and 4 mg/mL BSA
1-4 Stool sample treated with Buffer A and 11.25 mg/mL BSA

DETAILED DESCRIPTION

Definitions

To facilitate an understanding of the present invention, a number of terms and phrases are defined below. Additional definitions are set forth throughout the detailed description.

As used herein, "a" or "an" or "the" can mean one or more than one. For example, "a" pen can mean one pen or a plurality of pens.

As used herein, an "interfering substance" means any atom, ion, molecule, compound, substance, or composition, or combination thereof, that acts to decrease the quantity and/or purity of nucleic acids extracted from a sample by a nucleic acid extraction and purification method, either directly or indirectly, with respect to the quantity and quality when the interfering substance is absent.

As used herein, an "inhibitor" means any atom, ion, molecule, compound, substance, or composition, or combination thereof, that acts to decrease the activity, precision, or accuracy of an assay, either directly or indirectly, with respect to the activity, precision, or accuracy of the assay when the inhibitor is absent.

As used here in, the term "impurity" means both interfering substance and inhibitor.

As used herein, the term "pre-treatment" means that prior to extraction of nucleic acids from a sample containing nucleic acids, said sample is mixed and incubated with a buffer, leading to precipitation of certain substances in said sample, followed by pelleting any precipitates and solid matter by centrifugation; thereafter the supernatant containing nucleic acids is transferred to another container to separate said supernatant from said pellet.

As used herein, an "binding protein" means any protein that binds the impurities in stool to form a complex, but itself does not interfere with the process of extracting nucleic acids.

As used herein, the term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. "PCR" generally involves the use of a nucleic acid sequence as a template for producing a large number of complements to that sequence. The template may be hybridized to a primer having a sequence complementary to a portion of the template sequence and contacted with a suitable reaction mixture including dNTPs and a polymerase enzyme. The primer is elongated by the polymerase enzyme, producing a nucleic acid complementary to the original template. For the amplification of both strands of a double stranded nucleic acid molecule, two primers may be used, each of which may have a sequence that is complementary to a portion of one of the nucleic acid strands. The strands of the nucleic acid molecules are denatured—for example, by heating—and the process is repeated, this time with the newly synthesized strands of the preceding step serving as templates in the subsequent steps. A polymerase chain reaction (PCR) amplification protocol may involve a few to many cycles of denaturation, hybridization and elongation reactions to produce sufficient amounts of the desired nucleic acid. Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "enzymatic-based assay or analysis" refers to any method of determining the quantity and nucleotide composition of nucleic acids of interest by using enzyme(s). For example, enzymatic-based assays include, but are not limited to, DNA sequencing methods, probe hybridization methods, polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); molecular beacon technology (e.g., U.S. Pat. No. 6,150,097, herein incorporated by reference in its entirety); ligase chain reaction (e.g., Barany Proc. Natl. Acad. Sci USA 88, 189-93 (1991), herein incorporated by reference in their entireties).

Embodiment of the Technologies

Stool comprises foods debris, digestive metabolites, and many other substances. As such, stool is the most complicated biological sample and contains a large amount of various impurities that interfere with nucleic acid extraction/purification and inhibit enzymatic-based analysis. Solid matter in stool can be removed by centrifugation, but soluble impurities such as bile and polyphenols remain in solution containing DNA, interfering with DNA extraction and inhibiting enzymatic-based analysis. In some prior arts, CTAB precipitation and phenol/chloroform extraction were used to remove impurities. In another prior art, PPVP particles were used to bind and react with soluble impurities like polyphenols. However, these methods are either not highly effective or too complicated to use. It is known that some soluble proteins like albumin can bind many molecules and act as carriers and transporters in blood. In prior arts, the low concentration of BSA or T4 gene 32 protein (gp32) was added to the PCR system to reduce the inhibitory effects. However, this measure is not enough to eliminate the inhibitory effect when DNA is extracted from stool. Moreover, adding BSA in PCR reaction (after DNA extraction/purification) cannot remove the impurities that interfere with DNA extraction/purification.

In the current invention, we provide a method that introduces the binding protein(s) into the stool sample itself before or during the process of extracting nucleic acids to facilitate purification of nucleic acids from highly complicated stool. In one preferred embodiment, the binding protein(s) can bind to impurities in stool, but itself will not interfere with the process of extracting nucleic acids. When a large amount of the binding protein is added to the stool sample, substantial amounts of impurities will be bound to the binding protein(s) added. As a result, fewer impurities will interfere with extraction of nucleic acids, improving the efficiency of isolating nucleic acids from stool. In the same way, fewer impurities will be co-isolated, yielding highly concentrated, highly purified nucleic acids for analysis. In some embodiments, said nucleic acids are DNA and any forms of RNAs, including, but not limited to, mRNA, fRNA, tRNA, microRNA, small interfering RNA (siRNA), or any combination of them.

In some embodiments, this provided method is especially useful when the magnetic bead-based methods such as sequence-specific capture are used to retrieve nucleic acids from stool. This is because some of impurities in stool can bind to magnetic beads, reducing its effectiveness of capturing nucleic acids. Moreover, when the impurities bind to the beads, they will be co-eluted when captured nucleic acids are eluted off from the beads, inhibiting subsequent enzymatic-based analysis. However, when enough amounts of the binding proteins are added to the stool sample, they will absorb many of the impurities, minimizing the amount of impurities that can adversely affect the magnetic bead-based nucleic acid extraction methods. This invention is especially useful when a large stool is required to be converted into highly concentrated nucleic acids.

In some preferred embodiments, one of the preferred binding proteins is bovine serum albumin (BSA). In some embodiments, BSA is added to the stool sample before or during the process of using sequence specific capture to retrieve nucleic acids. BSA can minimize the amount of the impurities that interfere with sequence specific capture and reduce the quantity of the inhibitors that can be co-isolated with nucleic acids. In general, the more BSA is added, the better the removal result is. In some embodiments, the final concentration of BSA in the stool solution, from which nucleic acids are extracted, is at least 1 mg/mL; In some embodiments, the final concentration of BSA in the stool solution is at least 5 mg/mL; In some embodiments, the concentration of BSA in the stool solution is at least 10 mg/mL; In some preferred embodiments, the final concentration of BSA in the stool solution is at least 11.25 mg/mL; It is obvious that the current invention will not be limited to BSA. In some embodiment, said binding protein(s) for facilitating extraction and purification of nucleic acids from stool are any protein(s) that can bind the impurities in stool, but itself does not interfere with nucleic acids extraction.

In some cases, the use of the binding proteins alone may not able to completely remove the impurities in stool. The current invention also provides a method that combines the method of using binding protein(s) with another method to further improve removal of impurities in stool. In one preferred embodiment, the binding protein(s) is added to the stool sample before, during, or after performing said another method. In some embodiment, said another method uses a pre-treatment buffer to treat the stool sample before DNA extraction. In one preferred embodiment, said another method first mixes and incubates said pre-treatment buffer with said stool sample, leading to precipitation of impurities. Then, the precipitates are pelleted together with stool solid matter (if present) by centrifugation, yielding supernatant containing nucleic acids. Thereafter, the supernatant is separated from the pellet by transferring the supernatant to another tube (liquid container). DNA is extracted from the transferred supernatant by sequence-specific capture.

In some embodiments, said pre-treatment buffer contains both acetate salt(s) and guanidine thiocyanate, wherein acetate salt(s) is, but not limited to sodium acetate, potassium acetate, ammonium acetate, lithium acetate, other soluble acetate salts, or any combination of them. In some embodiments, final concentration of said acetate salt(s) is 50 mM or more after mixing said pre-treatment buffer with said stool sample. In some embodiments, the final concentration of the acetate salt(s) is 100 mM or more after mixing said pre-treatment buffer with said stool sample. In some embodiments, the final concentration of the acetate salt(s) is 200 mM or more after mixing said pre-treatment buffer with said stool sample.

In another preferred embodiment, the final concentration of guanidine thiocyanate is from about 2.0M to 3.0M after mixing the pre-treatment buffer with the stool sample. In another embodiment, the pre-treatment buffer itself serves as the hybridization buffer for sequence specific capture. As a result, there is no need for additional solution for hybridization. In some preferred embodiments, guanidine thiocyanate improves lysis of stool and protects DNA from degradation during the process of extracting DNA from stool.

The current invention also embodied a system that contains minimized steps for nucleic acid extraction and purification from stool. The system includes only one centrifugation step to remove solid matter (if present) from sample along with precipitated impurities and inhibitors. In some embodiments, the system also provides automated nucleic acids preparation using sequence specific capture with the oligonucleotide probe conjugated magnetic beads. In some preferred embodiments, nucleic acids from 0.5 gram or more of stool are extracted, purified, and eluted into as little as, for example, 40 µL elution buffer, wherein the eluted nucleic acid preparation is ready for enzymatic-based analysis without detectable inhibitory effects. In some embodiments, the nucleic acid targets that are captured by oligonucleotide probe conjugated magnetic beads, are used directly in enzymatic-based analysis assays without eluting them off the beads.

The current invention is especially useful to preparation of highly concentrated and purified nucleic acids with a small final elution volume from a large amount (volume) of stool. Adding the binding proteins to stool will not interfere with sequence specific capturing target DNA sequences from stool, nor will it add additional steps for removal of impurities. In some embodiments, the binding protein(s) is added to the stool sample together with the pre-treatment buffer before centrifugation of solid matter and precipitates to produce a more clarified supernatant containing nucleic acids. In some embodiments, the binding protein(s) is added to the stool sample after the step of centrifugation. In some embodiments, the binding protein(s) is added to the stool sample before denaturing of sample. In some embodiments, the binding protein(s) is added to the stool sample after denaturing of the stool sample.

The current invention also embodied a system that contains minimized steps for nucleic acid recovery and purification from crude biological samples like stool. The system includes only one centrifuge step to remove solid particles (if present) from a crude stool sample as well as any precipitated impurities. In some embodiments, the system also provides automated nucleic acids preparation using sequence specific capture with oligonucleotide probe conjugated magnetic beads. In some embodiments, the binding protein(s) such as BSA is used during the nucleic acids preparation process. In some embodiments, some of the impurities are precipitated and removed before and/or the nucleic acid extraction process. The entire impurity removal process is seamlessly integrated into the system, where no extra step is introduced. In some preferred embodiments, nucleic acids from 0.5 gram or more of stool is extracted, purified, and eluted into as little as, for example, 40 µL elution buffer, wherein the eluted nucleic acids preparation is ready for PCR without detectable inhibitory effects. In some preferred embodiments, nucleic acids targets from more than one gram of stool are extracted, purified, and eluted, wherein the eluted nucleic acids preparation is ready for PCR without inhibitory effects. In some embodiments, nucleic acids sequences captured by oligonucleotide probe conjugated magnetic beads are used directly in following enzymatic-based analysis assays without elution of them off from the beads.

The current invention also embodied a kit for impurity removal from crude samples like stool. The kit contains a pre-treatment buffer, binding protein(s), tubes and instruction of use. This kit is most useful when it combines with the sequence-specific capture method for extraction and purification of specific target nucleic acid sequences from a large amount of crude stool sample, wherein the resulting nucleic acid preparation is in a small volume and contains minimum amounts of impurities, making it possible to load sufficient amounts of highly purified nucleic acids into enzymatic-based assays for analysis. Any suitable tubes from commonly available suppliers can be included in the kit.

EXPERIMENTS

Example 1

Stool sample is collected from a male adult volunteer. About 15 grams of stool sample is placed in a tube containing 30 mL of preservation buffer developed by GLC Biotechnology, Inc. After homogenization, 20 mL portion of homogenized stool is mixed 1:1 with stool treatment and hybridization buffer A, which contains 5M guanidine thiocyanate, 100 mM sodium acetate, 200 mM potassium acetate, 100 mM Tris, and pH is adjusted to about 8.5. After thorough mixing, the mixtures are incubated under room temperature for 2 hours before being centrifuged at 10800×g for 20 minutes. After centrifugation, supernatants are aliquoted into 4 mL portions (equivalent to 1 gram of stool each) for DNA extraction.

Four different conditions were tested. Condition 1: no bovine serum albumin (BSA) was added to a supernatant aliquot created above. Condition 2: the concentrated bovine serum albumin (BSA) solution was added to the second supernatant aliquot with a final BSA concentration of 1 milligram per milliliter (1 mg/mL). Condition 3: the concentrated bovine serum albumin (BSA) solution was added to the third supernatant aliquot with a final BSA concentration of 4 milligram per milliliter (4 mg/mL). Condition 4: the concentrated bovine serum albumin (BSA) solution was added to the fourth supernatant aliquot with a final BSA concentration of 11.25 milligram per milliliter (11.25 mg/mL). After BSA was added and thoroughly mixed, each aliquot was heated at 95° C. for 10 minutes to denature DNA.

The denatured samples were then loaded into a deep-well plate, where each well contained 20 μL oligonucleotide probe conjugated magnetic beads. Sequence specific capture was then performed on an automated instrument platform, where sequence specific capture with oligonucleotide probe conjugated magnetic beads (hybridization for capturing target DNA sequences), beads collection and transfer, beads washing, and DNA elution were all performed automatically without further human intervention. Captured stool DNA sequences were eluted in a tris buffer with a concentration of 5 mg stool equivalent per microliter (5 mg/μL), which was ready to use in PCR. In this experiment, a sequence of human beta-gene (ACTB) was captured by sequence-specific capture.

The ACTB sequence captured from each stool supernatant aliquot was evaluated by real-time qPCR. The PCR condition is described as below: Precision-melt HRM Master Mix (final concentration 1×, Biorad), primers (final concentration 0.5 μM, the sequences of the forward and reverse primers are: 5'-TTGCTTTTTCCCAGATGAGC-3' (SEQ ID NO 1) and 5'-ACACTCCAAGGCCGCTTTAC-3', (SEQ ID NO 2) respectively), and the DNA extracted (equivalent to 20 mg stool) were mixed and the total PCR volume was adjusted to 20 μL with nuclease free water. Real-time qPCR was performed on Light-cycler 480 II real-time cycler (Roche). The qPCR protocol is described as below: 95° C. for 10 min, followed by 50 cycles of 95° C. for 20 seconds, 60° C. for 30 seconds, and 72° C. for 45 seconds, followed by a 72° C. extension for 3 minutes. And then a high-resolution-melting (HRM) melting curve is generated for quality control with the following settings: 95° C. for 1 minute, 60° C. for 1 minute, then a melting curve was obtained from 60° C. to 95° C. with an increment of 0.02° C./second and 25 acquisitions/° C. The final results are analyzed with Light-cycler 480 software from Roche.

FIG. 1 demonstrated the results of real-time qPCR analysis of the captured ACTB sequences. In a real-time PCR reaction without any inhibitory effects, a smaller cycle number reflects a higher amount of input DNA. However, the cycle number will become larger or no amplification will be observed if there are inhibitors present in the PCR system. In this experiment, ACTB sequences were extracted from four aliquots under the same condition, except for that each of the four aliquots was treated with different amounts of BSA. As seen from FIG. 1, the cycle number clearly correlates with the amount of BSA that was used to treat aliquoted stool solution. The more BSA was added, the smaller the cycle number is. This result clearly indicates that the presence of BSA improved isolation of target ACTB sequences by sequence specific capture. The reason that the presence of BSA improved isolation of DNA is that BSA can bind to the impurities present in the stool solution. Because many of the impurities are now bound to BSA, fewer impurities will interfere with DNA extraction and be co-isolated with DNA. As a result, the quantity and/or the purity (quality) of DNA extracted increase. In other words, the presence of BSA improves preparation of highly concentrated, purified DNA from the stool sample.

CITATION LIST

Patent Literature

Kary B. Mullis et al., U.S. Pat. No. 4,683,195 A 1986
Kary B. Mullis, U.S. Pat. No. 4,683,202 B1 1985
Kary B. Mullis et al., U.S. Pat. No. 4,965,188 A 1987
Michael S. Urdea et al., U.S. Pat. No. 5,849,481 A 1995
Michael S. Urdea et al., U.S. Pat. No. 5,710,264 A 1995
Michael S. Urdea et al., U.S. Pat. No. 5,124,246 A 1989
Michael S. Urdea et al., U.S. Pat. No. 5,624,802 A 1995
Paul M. Lizardi, U.S. Pat. No. 6,210,884 B1 1998
Paul M. Lizardi, U.S. Pat. No. 6,183,960 B1 1998
Sherman Weissman et al., U.S. Pat. No. 6,235,502 B1 1999
Sanjay Tyagi et al., U.S. Pat. No. 6,150,097 A 1997
Janelle J. Bruinsma et al., US 2012/0288957 A1 2012
Janelle J. Bruinsma et al., US 2012/0288868 A1 2012
Micheal J. Domanico et al., US 2012/0285900 A1 2012

Non-Patent Literature

BARANY F., "Genetic disease detection and DNA amplification using cloned thermostable ligase", Proc Natl Acad Sci USA. 1991 Jan. 1; 88(1):189-93.
ATSUSHI AKANE et al., "Indentification of the Heme Compund Copurified with Deoxyribonucleic Acid (DNA) from Bloodstains, a Major Inhibitor of Polymerase Chain Reaction (PCR) Amplification", Journal of Forensic Sciences, JFSCA, Vol. 39, No. 2, March 1994, pp. 362-372
CAROL A. KREADER, "Relief of Amplification Inhibition in PCR with Bovine Serum Albumin or T4 Gene 32 Protein", Applied and Environmental Microbiology, March 1996, Vol. 62, No. 3, p. 1102-1106
WALEED ABU AL-SOUD et al., "Purification and Characterization of PCR-Inhibitory Components in Blood Cells", Journal of Clinical Microbiology, February 2001, p. 485-493

What is claimed is:

1. A method for preparation of purified nucleic acids from stool sample comprises the step of using binding protein(s) to deplete impurities in said stool sample, wherein said binding protein(s) is added to said stool samples before or during said preparation of said purified DNA from said stool sample.

2. The method of claim 1, wherein said nucleic acids are, but not limited to, DNA, mRNA, fRNA, tRNA, microRNA, small interfering RNA (siRNA), or any combination of them.

3. The method of claim 1, wherein said binding protein(s) is the protein(s) that binds said impurities in said stool sample, including, but not limited to, albumin, acetylated albumin, bovine serum albumin (BSA), human serum albumin (HSA), casein, beta casein, T4 gene 32 protein (gp32), or any combination of them.

4. The method of claim 1, wherein said preparation of said purified nucleic acids from said stool sample is, but not limited to, sequence-specific capture, carboxylate modified magnetic beads capture, silica based nucleic acid extraction and purification, alcohol precipitation, or any combination of them.

5. A method of preparing purified DNA from a stool sample comprises steps of:
  (a) treating said stool sample with a pre-treatment buffer, wherein said pre-treatment buffer is first mixed and incubated with said stool sample to precipitate impurities in said stool sample, followed by centrifugation to pellet the precipitates and other solid matter to create supernatant containing said DNA; then, the supernatant is separated from the pellet by transferring said supernatant to another liquid container; and
  (b) adding binding protein(s) to said stool sample before, during, or after said step (a); and
  (c) capturing target DNA sequences from said transferred supernatant by sequence specific capture with magnetic beads that utilizes said pre-treatment buffer as the hybridization buffer.

6. The method of claim 5, wherein said pre-treatment buffer contains acetate salt(s) and guanidine thiocyanate.

7. The method of claim 6, wherein the concentration of said acetate salt(s) in said stool sample is 50 mM or more, 100 mM or more, and 200 mM or more after mixing said pre-treatment buffer with said stool sample.

8. The method of claim 6, wherein the concentration of said guanidine thiocyanate in said stool sample is 2.0M or more after mixing said pre-treatment buffer with said stool sample.

9. The method of claim 6, wherein said binding protein(s) is bovine serum albumin (BSA).

10. The method of claim 9, wherein the concentration of said BSA in said stool sample is 1 mg or more per 1 mL said stool sample.

* * * * *